United States Patent
Gauchet et al.

(10) Patent No.: US 6,579,320 B1
(45) Date of Patent: Jun. 17, 2003

(54) INTERVERTEBRAL DISC PROSTHESIS WITH CONTACT BLOCKS

(75) Inventors: Fabien Gauchet, Duvy (FR); Pierre-Henri Saint-Martin, Pessac (FR); William Kelly, Montville, NJ (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/857,663

(22) PCT Filed: Dec. 9, 1999

(86) PCT No.: PCT/FR99/03075

§ 371 (c)(1),
(2), (4) Date: Jul. 20, 2001

(87) PCT Pub. No.: WO00/35387

PCT Pub. Date: Jun. 22, 2000

(30) Foreign Application Priority Data

Dec. 11, 1998 (FR) .............................................. 98 15674
Jul. 22, 1999 (FR) .............................................. 99 09522

(51) Int. Cl.[7] ................................................ A61F 2/44
(52) U.S. Cl. .................................................. 623/17.15
(58) Field of Search ........................... 623/17.11, 17.13, 623/17.15, 17.16

(56) References Cited

U.S. PATENT DOCUMENTS

| 4,946,378 | A |   | 8/1990  | Hirayama et al. |        |
|-----------|---|---|---------|-----------------|--------|
| 5,370,697 | A | * | 12/1994 | Baumgartner     | 623/17 |
| 5,458,642 | A | * | 10/1995 | Beer et al.     | 623/17 |
| 5,534,030 | A |   | 7/1996  | Navarro et al.  |        |
| 5,674,294 | A |   | 10/1997 | Bainville et al.|        |
| 5,824,094 | A | * | 10/1998 | Serhan et al.   | 623/17 |
| 6,019,793 | A | * | 2/2000  | Perren et al.   | 623/17 |

FOREIGN PATENT DOCUMENTS

EP           0 356 112       2/1990

\* cited by examiner

*Primary Examiner*—Eduardo C. Robert
(74) *Attorney, Agent, or Firm*—Lerner, David, Littenberg, Krumholz & Mentlik, LLP

(57) ABSTRACT

An intervertebral disk prosthesis comprising two plates and a cushion interposed between the plates is contemplated. The cushion includes a compressible body having two ends in contact with the plates. At least one of the plates comprises at least one stud for stressing the body along a direction not parallel to a main access of the prosthesis and mobile relative to the body. Thus the prosthesis imitates and approximates the mechanical properties of a healthy natural intervertebral disk.

21 Claims, 4 Drawing Sheets

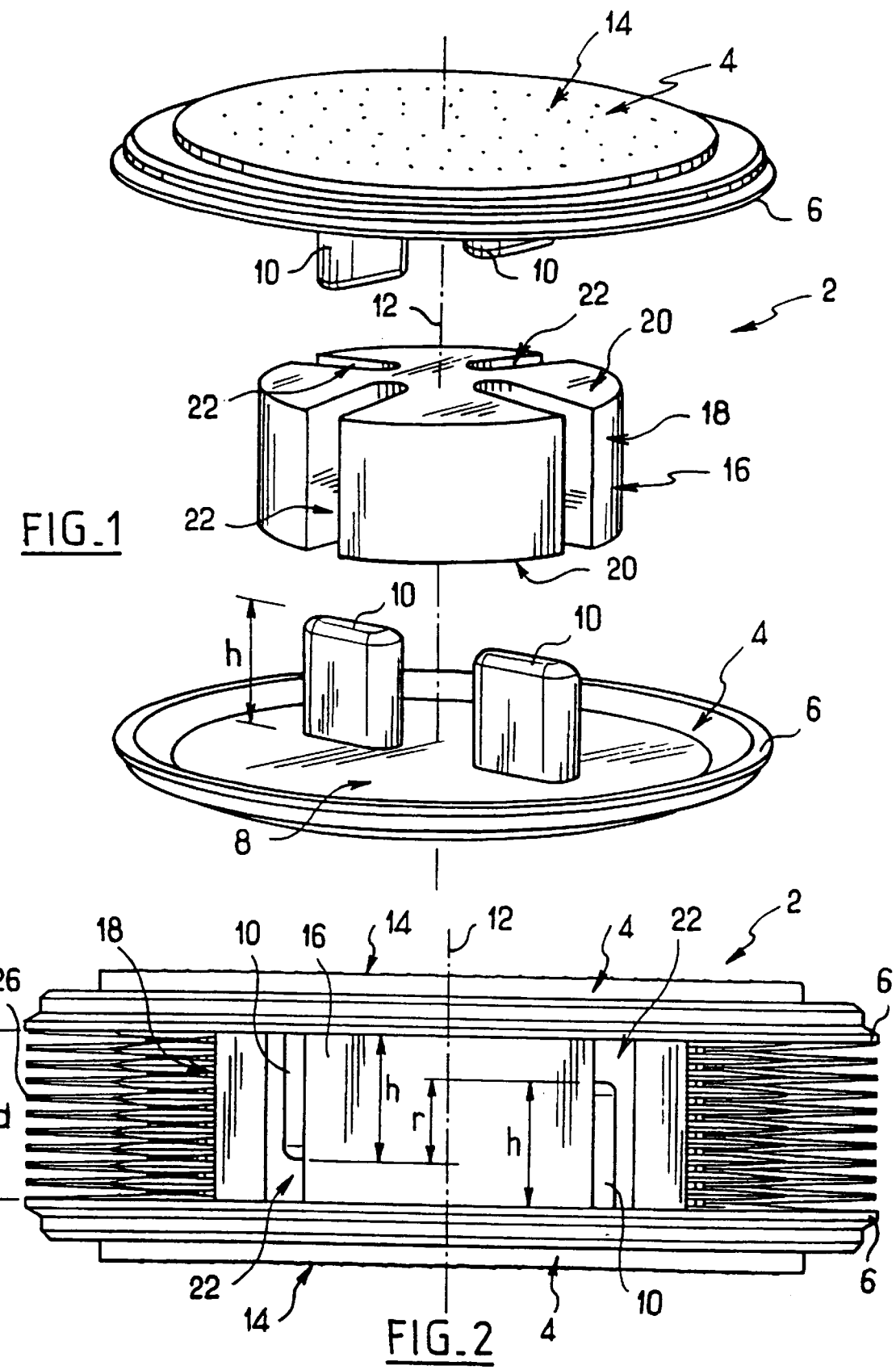

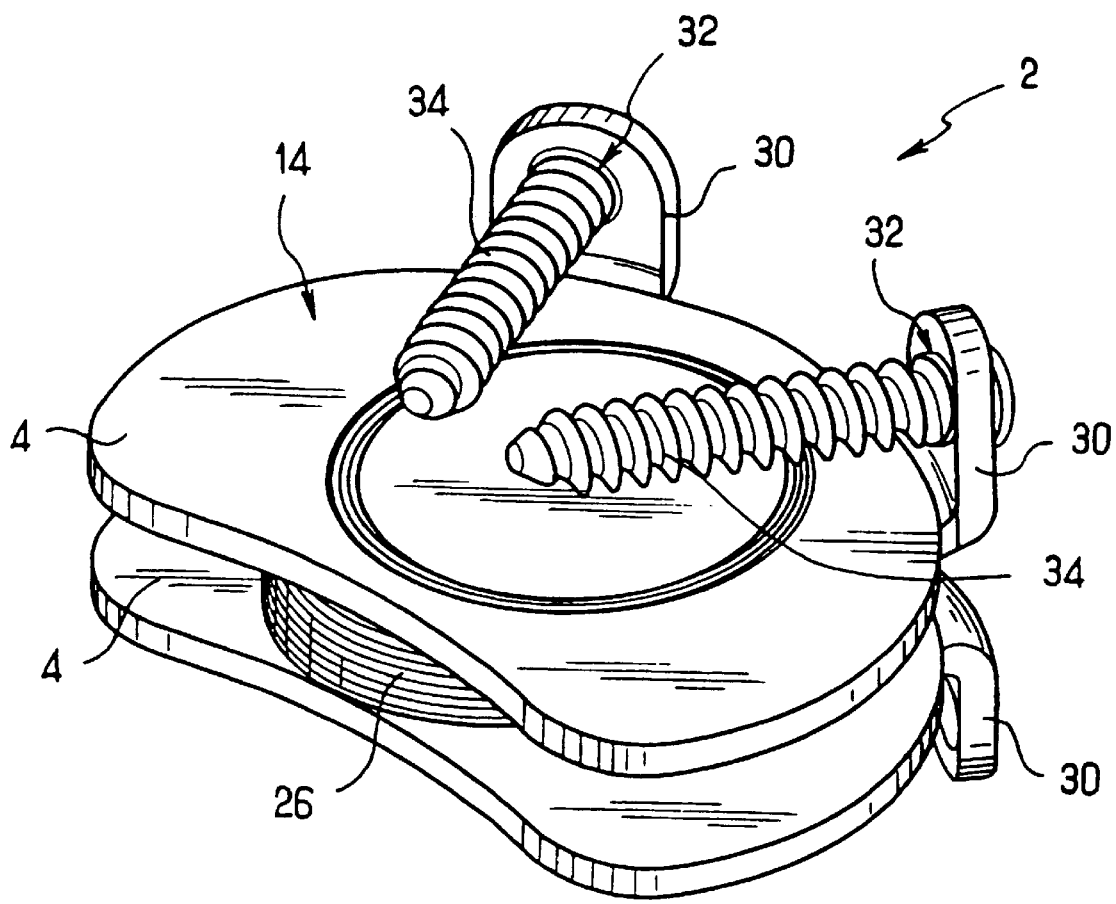
FIG_3

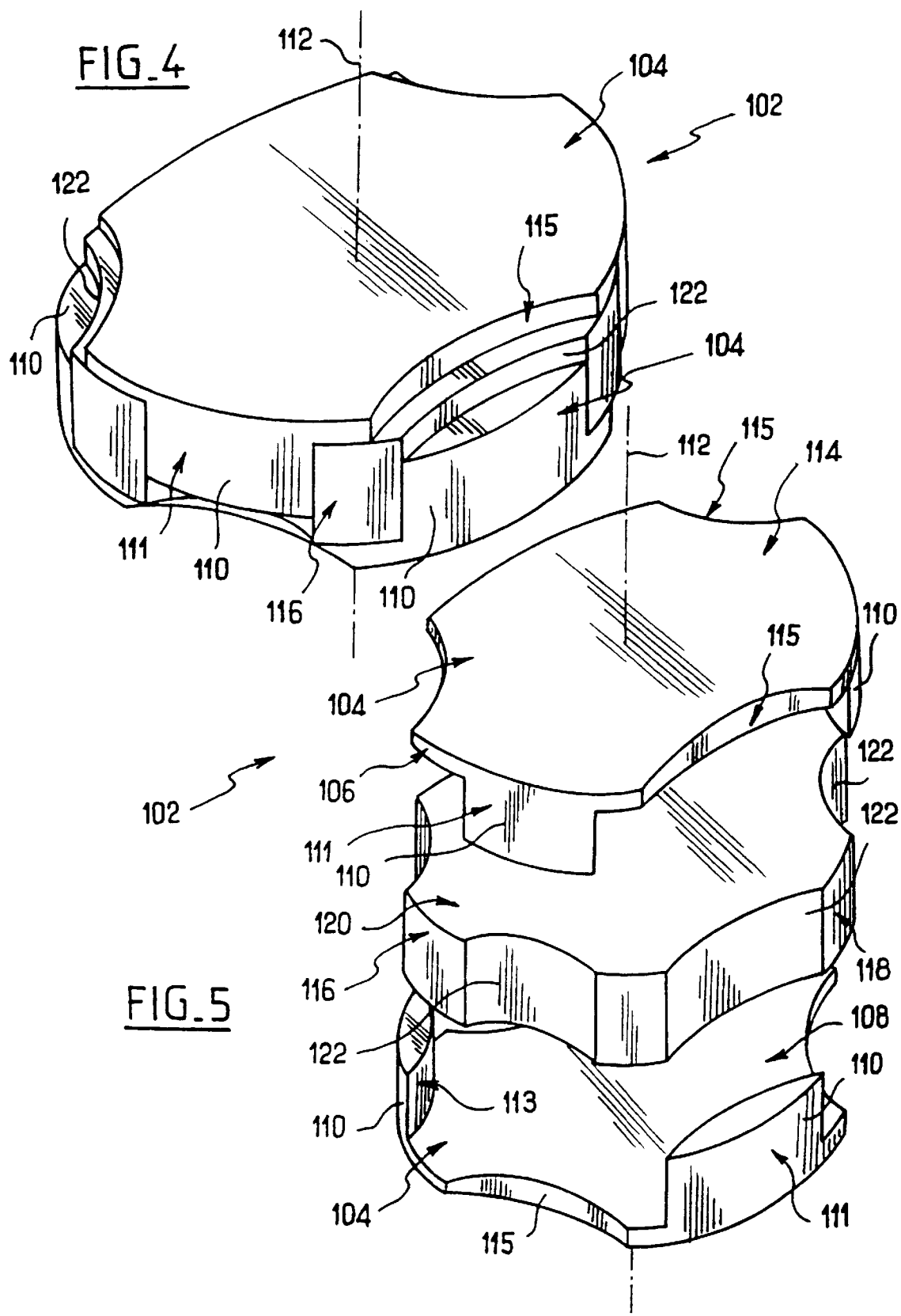

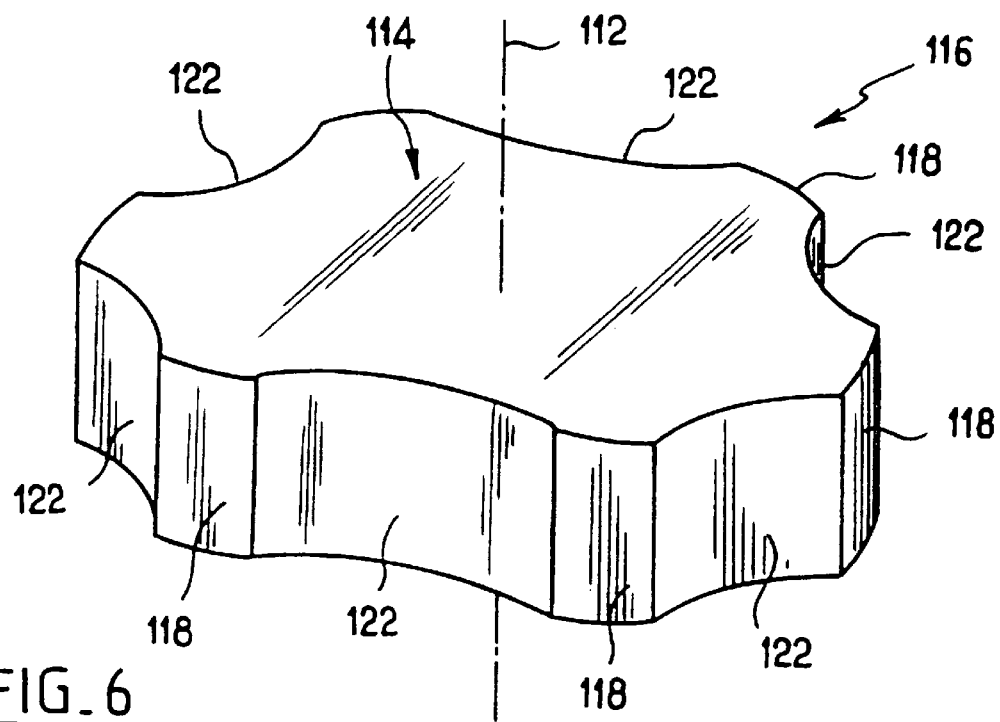
FIG_6
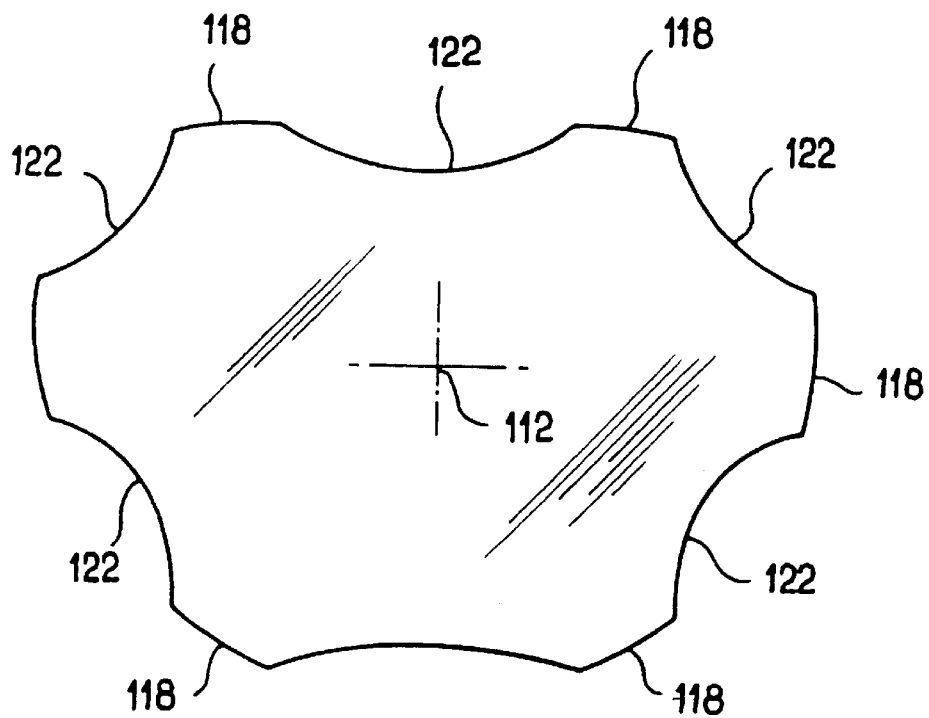
FIG_7

INTERVERTEBRAL DISC PROSTHESIS WITH CONTACT BLOCKS

FIELD OF THE INVENTION

The invention concerns intervertebral disc prostheses.

BACKGROUND OF THE INVENTION

European Patent 0 356 112 discloses a prostheses comprising two plates and a body of compressible material interposed between and fixed to the plates. The prosthesis replaces the natural disc after the disc has been ablated, with the plates bearing against the vertebral plates of the adjacent vertebrae. With such prostheses it is possible to a great extent to reproduce the mechanical behavior of a healthy natural disc, in particular in compression or in torsion about any axis perpendicular to the longitudinal direction of the spine. However, the prostheses do not satisfactorily imitate two other movements: the relative rotation of the two plates about a main axis of the prosthesis or the axis of the spine, and the relative displacement of the two plates by shearing or sliding in a plane perpendicular to this axis. For these two movements, the known prostheses offer an insufficient mechanical reaction and are too rigid for the first movements.

It is therefore an object of the invention to more closely imitate the behavior of a healthy natural intervertebral disc.

The invention provides an invertebral disc prothesis comprising two plates and a deformable body interposed between the plates, where at least one of the plates comprises at least one contact stud which is able to stress the body in a direction not parallel to a main axis of the prosthesis and is movable relative to the body.

The invention also provides an intervertebral disc prosthesis comprising two plates and a deformable body interposed between the plates, where at least one of the plates comprises at least one contact stud which is movable in the body.

Thus, the contact stud offers mechanical resistance when the prosthesis is subjected to a rotational stress about its main axis or a shearing stress in a direction perpendicular to this axis. In addition, this resistance is variable depending on the relative position of the plates, for example depending on how close they are to each other and/or how inclined they are relative to each other. Indeed, the resistance to shearing and to rotation mentioned above will be greater the closer the contact stud is to the opposite plate and thus the more compressed the body is on the axis. Moreover, depending on the position of the contact stud, a relative inclination of the plates will bring the contact stud closer to the opposite plate and thus increase the resistance of the prosthesis locally near the contact stud. In contrast, the further away the contact stud is from the opposite plate the more the resistance is reduced. The prosthesis thus has a mechanical behavior which varies depending oh the relative position of the plates, which makes it similar to a healthy natural disc. If its dimensions are sufficiently great, the contact stud or each contact stud can additionally constitute an abutment limiting one of the relative movements of flexion or translation of the plates. Of course, what has just been described above for one contact stud is valid a fortiori when the prosthesis comprises a plurality of contact studs.

The contact stud is advantageously offcentered relative to the plate which bears it.

Thus, the resistance behavior of the prosthesis largely depends on the axis of the flexion and on the direction of this flexion.

The contact stud advantageously extends at a distance from the plate other than the one which bears it when the prosthesis is not stressed.

The contact stud advantageously has a length of between about 0.60 d and about 0.90 d, where d is a distance separating the two plates when the prosthesis is not stressed.

Advantageously, for the plate or each plate provided with at least one contact stud, the body is immobilized relative to the plate, in respect to a displacement parallel to the plate, only by virtue of the contact stud.

Thus, the body bears, without anchoring, on the plate or each plate comprising a contact stud. Assembly is thus carried out simply by stacking the plates and the body together. The body is, in particular, able to be separated from the plate under the effect of traction causing a displacement in the direction away from the plate, which is not conceivable in the normal conditions of use of the prosthesis.

The contact stud advantageously extends in a recess of the body opening into a lateral face of the body.

The contact stud advantageously has a flattened shape in a plane radial to the main axis of the prosthesis.

Thus, in the event of shearing or torsion about the main axis of the prosthesis, the bearing surface between the contact stud and the body is considerable, resulting in good distribution of the load, although the volume of the contact stud can be relatively small.

The contact stud advantageously has a flattened shape in a plane tangential to a direction circumferential to the main axis of the prosthesis.

The contact stud advantageously has a cylindrical lateral face, and the body has a cylindrical face bearing on the cylindrical face of the contact stud.

The contact stud advantageously has a lateral face extending outside the body.

Thus, the contact stud encroaches moderately on the volume of the body.

The lateral face of the contact stud advantageously extends in the continuation of an outer lateral face of the body.

Advantageously, for the contact stud or each contact stud, the plate other than the one bearing the contact stud has a recessed zone constituting the part facing the contact stud when the prosthesis is at test.

Thus, in the event of flexion or of the plates coming extremely close to each other, the contact stud or each contact stud does not come into abutment against the opposite plate, so that the deformable body taking up the stresses continues to impose the mechanical behavior of the prosthesis.

The plate advantageously comprises at least two contact studs arranged symmetrically about a center of the plate.

Each plate advantageously comprises at least one contact stud, the contact studs overlapping in a direction parallel to the main axis of the prosthesis when the prosthesis is not stressed.

The anti-shearing effect is increased in this way.

The contact studs advantageously overlap by a length of between about 0.35 d and about 0.65 d, where d is a distance separating the two plates when the prosthesis is not stressed.

Advantageously, when the prosthesis is not stressed, the contact studs overlap by a length of between about 0.45 h and about 0.85 h, where h is a height of the contact studs parallel to the main axis of the prosthesis.

Each plate advantageously comprises at least two contact studs, the contact studs being arranged alternatingly around the main axis of the prosthesis.

Other characteristics and advantages of the invention will also become apparent from the following description of two preferred embodiments given as nonlimiting examples.

BRIEF DESCRIPTION OF THE DRAWINGS

FIG. 1 is an exploded perspective view of a prosthesis according to a first preferred embodiment, without its bellows;

FIG. 2 is a side view of the prosthesis from FIG. 1, partially cut away in the area of the bellows;

FIG. 3 is a perspective view of an alternative to the prosthesis of the first embodiment;

FIGS. 4 and 5 are perspective views of a prosthesis according to a second preferred embodiment, in the assembled state and in an exploded representation, respectively; and FIGS. 6 and 7 are perspective and plan views, respectively, of the body of the prosthesis in FIG. 4.

DETAILED DESCRIPTION OF THE INVENTION

Referring to FIGS. 1 and 2, an intervertebral disc prosthesis 2 is shown. The intervertebral disc prosthesis 2 is intended for the lumbar region of the spine.

The prosthesis 2 comprises two plates 4 which are identical to each other. Each plate 4 has a generally planar disc shape. In the present embodiment, each plate has a slightly raised peripheral edge 6 projecting from a plane central inner face 8, thus giving it the appearance of a saucer.

Each plate comprises contact studs 10, preferably two identical contact studs. Each contact stud 10 has the general shape of a rectangular pipe with one edge in contact with the plate, and the other edge rounded. The height and width of the contact stud are about equal, but the thickness is substantially smaller. The contact studs 10 project perpendicularly from the inner face 8 and are arranged symmetrically with respect to a main axis 12 of the prosthesis passing through the center of the face 8. The contact studs 10 are substantially perpendicular to the face 8 when not stressed. The thickness of the contact studs 10 extends in a plane radial to the axis 12 so that the two contact studs are substantially in the same radial plane, either side of the axis 12. On a plane outer face 14, the plate has reliefs making it easier to fix the plate 4 to a vertebral plate, for example, by means of a hydroxyapatite covering. The plates can be made of metal or composite material.

The prosthesis comprises a body 16 of general cylindrical shape, having a cylindrical outer face 18 and two opposite plane end faces 20. The body 16 is here made of an elastic material such as an elastomer. The body defines channels or recesses 22, here four in number. The channels are profiled in a direction parallel to the axis 12 of the body 16. The profile is identical to the profile of the contact studs 10 in a plane transverse to the height of the contact studs 10 or the axis 12. Each channel 22 thus has a generally plane shape and extends in a radial plane to the axis 12. Each channel 22 extends at a distance from the axis 12 and opens out on the cylindrical face 18 across its entire height and on each of the two end faces 20. Viewed from the end, the body thus has a cross or cloverleaf shape.

For assembly, the body 16 is arranged between the two plates 4 which have their inner faces 8 and their contact studs 10 facing each other, the two plates being mutually offset by a quarter turn about the axis 12, the four channels 22 being in line with the four contact studs. The two plates 4 are moved toward each other until their inner faces 8 come into surface contact with the end faces 20 of the body, the four contact studs 10 penetrating the four respective channels 22. The four contact studs thus belong to the two plates alternately about the axis 12. The plates 4 bear on the body 16 without any anchoring other than the contact studs. The body 16 is immobilized by bearing on the inner faces 8 and the contact studs 10, the latter by themselves prohibiting its displacement in translation in a plane perpendicular to the axis 12.

The prosthesis comprises a compressible bellows 26 in the form of a sleeve which has a corrugated profile and is fixed to the edges 6 of the two plates in order to isolate the space to the inside of the bellows, including the body 16, from the outside. In this case, the bellows has ten convolutions, which creates nine crests in addition to the crests fixed to the edges 6. The bellows and the plates can be made of titanium or titanium alloy.

In FIG. 2, the prosthesis is illustrated in the unstressed state. Each contact stud 10 has, on the axis 12, a height h of between about 0.60 d and about 0.90 d, where d is a distance, taken between the edges 6, separating the two plates when the prosthesis is in the unstressed state. In the present case, h is equal to about 0.75 d.

In one embodiment, the contact studs 10 of one plate partially overlap the contact studs 10 of the other plate as shown in FIG. 2. Thus, any cut through the prosthesis transverse to the axis 12 intercepts two contact studs 10 of the same plate 4 in the vicinity of the end faces 20, and the four contact studs in a median portion of the body. The length of overlap r, measured parallel to the axis 12, can be between about 0.35 d and about 0.65 d or between about 0.45 h and about 0.85 h. Here, r is equal to about 0.66 h and about 0.5 d.

Once fitted, the prosthesis behaves as follows.

If the prosthesis is subjected to rotation about the axis 12, the contact studs 10 cooperate with the body 16 in order to take up a large part of the generated stresses, which locally are shearing stresses.

If the prosthesis is compressed on its axis 12, the four contact studs 10 each penetrate further into their channel 22, moving in the direction of the opposite plate. The resistance of the prosthesis to shearing perpendicular to the axis 12 or to rotation about this axis is therefore greater.

If the prosthesis is subjected to flexion about an axis perpendicular to the axis 12, the two plates 4 incline relative to each other, which corresponds locally to a compression on certain parts of the body 16 and to a traction on other parts of the body. The resistance to shearing is thus increased in the former and reduced in the latter.

Although the body 16 is deformable, the movement of each contact stud 10 in its channel 22 is on the whole similar to a sliding movement.

Referring to FIG. 3, it is possible for each plate 4 to have two lugs 30 projecting from the outer face 14 of the plate 4 perpendicular to the plane of the plate. Each lug 30 has an orifice 32 passing right through it in the direction of the center of the plate and an identification of spherical shape on a face of the lug directed away from the plate. The orifices 32 can receive a bone screw 34 having a head whose lower face has a male spherical shape interacting with the female indentation of the lug 30 in order to permit free orientation of the screw relative to the associated lug.

For short-term anchoring of the disc prosthesis in the column, the screws 34 can be anchored in the body of the vertebrae adjacent to the disc which is to be replaced.

However, it will be possible to provide for long-term anchoring in which, in addition, the surfaces 14 of the plates 4 in contact with the adjacent vertebrae are covered with hydroxyapatite or any other substance known per se for stimulating bone growth. Before being covered, said surfaces can be treated to obtain a more or less porous surface condition, with anchoring points for the bone tissue, so as to ensure a better interface with said bone tissue. In FIG. 3, the plates have the shape of a bean with a posterior hilum.

FIGS. 4 to 7 illustrate a second embodiment in which the elements analogous to those of the first embodiment bear reference numbers increased by one hundred.

In this prosthesis 102, each of the two plates 104 here bears three contact studs 110. Each contact stud 110 is contiguous with the edge 106 of the plate and has a flat shape parallel to this edge, or substantially in a plane tangential to a direction circumferential to the axis 112. At the location of the contact studs 110, the edge 106 has a plane of substantially circular convex shape, each contact stud 110 has a convex cylindrical shape with an outer lateral face 111 intended to be set opposite the body 116 extending in the continuation of the edge 106. Each contact stud 110 additionally has an inner lateral face 113, also of convex cylindrical shape. The two cylindrical faces 111, 113 of each contact stud form two ridges parallel to the axis 112. The ridges slightly pronounced and very rounded (in a plane perpendicular to the main axis) in order to ensure that they do not cut into the body. The same is true of the ridges forming the free end face of the contact studs. Here once again, the contact studs of the two plates are intended to partially overlap parallel to the axis 112 so that the contact studs of the two plates mesh.

The body 116 has a lateral face 118 of generally cylindrical shape, except that its plane has the shape of a bean with posterior hilum. This is also the shape of the plane of the overall prosthesis. The six channels or seats 122 for contact studs on the body 116 are here delimited by cylindrical and concave faces, respectively, with axes parallel to the axis 112 and opening in the lateral face 118. The body 116 thus has laterally an alternating sequence of concave cylindrical faces 122 and convex cylindrical faces 118. Each face 122 has the same radius and the same length as the inner lateral face 113 of the corresponding contact stud in order to ensure surface contact of one with the other. However, the cylindrical face 122 of the body is higher than the contact stud, parallel to the axis 112.

Since the prosthesis is bean shape of the prosthesis and each contact stud is intended to be received between two contact studs of the other plate, the two plates are not strictly identical.

The prosthesis is assembled as before by bringing the two plates 104 toward one another with their contact studs 110 facing each other. The body 116 is interposed between the two plates 104. Each contact stud 110 thus penetrates into its seat 122, the lateral inner face 113 of the contact stud coming into contact with the face 122 of the channel. Once assembly has been completed, as in FIG. 4, each plate has its plane inner face bearing on the respective plane end face of the body.

The curvatures of the outer lateral faces 111 of the contact studs and the curvatures of the lateral face 118 of the body are chosen in such a way that the faces extend without any protruding or recessed ridges, giving the plane of the prosthesis a bean shape.

Each plate 104 has in a plane three recesses 115 in the edge 106, each delimited by a concave circular edge of greater radius than that of the associated face 122, as will be seen. Each recess 115 extends between two of the contact studs 110 of the plate so that said recess itself lies opposite a contact stud of the other plate.

Thus, in the assembled position, and at rest, as is shown in FIG. 4, each contact stud 110 extends opposite a part of the other plate formed by the recess 115. Thus, in the event of considerable stress displacing at least one of the contact studs 110 in the direction of the other plate, the contact stud can extend into the recess 115 without coming into abutment against the plate. The radius or the depth of the recess 115 is greater than that of the associated channel 122, which gives the assembly a step-shaped configuration locally and prevents any abutment of the contact stud against the opposite plate. This substantial depth of the recess increases the flexibility of the prosthesis in the event of torsion about an axis perpendicular to the main axis.

The dimensions r, h and d apply in this embodiment and have the same characteristics previously discussed. Also in this embodiment, it will be possible to provide a bellows or a screw attachment as in FIG. 3.

Here once again, each contact stud 110 is movable relative to the body and is able to stress the body in a direction not parallel to the axis 112, this stress being variable depending on the position of the contact stud in the body in the radial direction and the direction parallel to the axis 112. Although the contact studs penetrate less deeply into the body than in the preceding embodiment, they still ensure the transmission of the forces from the plates to the body.

The torisonal flexibility of the prosthesis can be regulated in particular by modifying the thickness of the three contact studs 110 since thicker contact studs make the prosthesis more rigid in torsion about the axis 112. Moreover, since there is no attachment between the body 116 and each of the plates 104, the latter can slide to a certain extent on the body during torsion. The body 116 arranged between the opposed contact studs 110 is compressed and pushed radially inward during torsion on account of the overall movement of the contact studs.

The axial rigidity of the prosthesis can be regulated in particular in the area of the contact zone between the body 116 and each plate 104. The inner face of each plate and the associated end face of the body can in fact be configured in such a way that the contact between these faces is established over a zone which becomes ever greater as the compression stress on the axis 112 increases. It will be possible, for example, to retain the plane shape of the end face of the body and give the inner face of the opposite plate a slightly spherical convex shape. The axial rigidity is in particular a function of the radius of the spherical face.

To ensure a long-term fixation between the plates and the body, the body is arranged to fit to a large extent between the contact studs of the plates. Since the plates are not rigidly fixed to the body production and regulation of the height of the prosthesis is facilitated before or during the intervention. In fact, in order to modify the height of the prosthesis itself, it suffices to modify the height of the body on the axis 112, for example by changing the body.

When the prosthesis is subjected to torsion about its main axis, the zones of the body situated between two successive contact studs are compressed in a circumferential direction. Since there are three contact studs here on each plate, there are three zones of compression. The torsional rigidity thus depends on the shape of the contact studs, the distance between the contact studs, and the extent of the axial overlap between the contact studs.

Each of the plates and also the body are made separately by injection molding.

The prosthesis tolerates prolonged cyclic loading without modification of its shape.

In some known prostheses, the joint between the plates and the body is fragile and risks rupturing. The prosthesis according to the invention eliminates this risk since the plates are designed to be movable by sliding on the body.

The contact studs limit the extension of the body beyond the contour of the plates, particularly during axial compression.

The body can have a spatially variable modulus of elasticity.

The body can be made of a number of materials.

When a homogeneous elastomer is used for the body, or an elastomer having the same modulus of elasticity everywhere, the ratio of the axial compression rigidity to the torsional rigidity is generally too high. To reduce the axial rigidity without reducing the torsional rigidity too much, one of the two following alternatives can be applied. First, the center of the body can be made of an elastomer which is less rigid than that of the periphery of the body. This reduces the compression rigidity without too much affecting the torsional rigidity since the latter is governed mainly by the periphery of the body. Second, a cavity can be formed in the inner surface of the plates in contact with the body, in order to reduce the surface of contact of the plates with the body. This reduces the volume of elastomer which is compressed in the event of axial compression, thereby diminishing the axial rigidity, but once again without too much affecting the torsional rigidity.

Many modifications can of course be made to the invention without departing from the scope thereof.

The contact stud 10, if there is only one per plate, can be at the center of the plate which bears it.

The contact stud or each contact stud 10, 110 can be in contact with the opposite plate 4, 104 when the prosthesis is not stressed or only when the compression of the prosthesis in the area of the contact stud exceeds a certain limit: the contact stud thus forms a stop limiting certain types of movements.

It is conceivable that only one of the plates 4, 104 will have one or more contact studs 10,110.

The body 16, 116 can be made of a viscoelastic material such as silicone.

The contact studs will be able to have another shape, for example a cylindrical shape with an axis parallel to the axis 12, 112.

The contact stud will be able to extend in the body within a seat which does not open out on a lateral face of the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Intervertebral disc prosthesis having a main axis, comprising:

two plates, wherein at least one of the plates includes at least one contact stud; and a deformable body interposed between the plates, wherein upon movement of the at least one of the plates having the at least one contact stud, the at least one contact stud stresses the body in a direction not parallel to the main axis of the prosthesis and the at least one contact stud is slidably movable relative to the body.

2. Intervertebral disc prosthesis having a main axis, comprising:

two plates; and a deformable body interposed between the plates, wherein at least one of the plates comprises at least one contact stud slidably movable in the body.

3. Prosthesis according to claim 1 or 2, wherein the at least one contact stud is located at an off-center position on the at least one plate.

4. Prosthesis according to claim 1 or 2, wherein the at least one contact stud extends from the at least one plate to a distance from the other plate when the prosthesis is not stressed.

5. Prosthesis according to claim 1 or 2, wherein the at least one contact stud has a length of between about 0.60 and about 0.90 of the distance separating the two plates when the prosthesis is not stressed.

6. Prosthesis according to claim 1 or 2, wherein the at least one contact stud immobilizes the body relative to the at least one plate so that no displacement parallel to the at least one plate occurs.

7. Prosthesis according to claim 1 or 2, wherein the at least one contact stud defines a flattened shape in a plane radial to the main axis of the prosthesis.

8. Prosthesis according to claim 1 or 2, wherein the at least one contact stud defines a flattened shape in a plane tangential to a direction circumferential to the main axis of the prosthesis.

9. Prosthesis according to claim 1 or 2, wherein a lateral face of the at least one contact stud extends continuously around an outer lateral face of the body.

10. Prosthesis according to claim 1 or 2, wherein the plate opposite the at least one plate including the at least one contact stud defines a recessed zone opposite the at least one contact stud when the prosthesis is at rest.

11. Intervertebral disc prosthesis having a main axis, comprising:

two plates, wherein at least one of the plates includes at least one contact stud;

a deformable body interposed between the plates, wherein upon movement of the at least one of the plates having the at least one contact stud, the at least one contact stud stresses the body in a direction not parallel to the main axis of the prosthesis and the at least one contact stud is movable relative to the body; and wherein the body defines a recess opening into a lateral face of the body and the at least one contact stud extends in the recess opening.

12. Intervertebral disc prosthesis having a main axis, comprising:

two plates, wherein at least one of the plates includes at least one contact stud;

a deformable body interposed between the plates, wherein upon movement of the at least one of the plates having the at least one contact stud, the at least one contact stud stresses the body in a direction not parallel to the main axis of the prosthesis and the at least one contact stud is movable relative to the body; and wherein the at least one contact stud has a cylindrical lateral face, and the body has a cylindrical face bearing on the cylindrical face of the at least one contact stud.

13. Intervertebral disc prosthesis having a main axis, comprising:
   two plates, wherein at least one of the plates includes at least one contact stud;
   a deformable body interposed between the plates, wherein upon movement of the at least one of the plates having the at least one contact stud, the at least one contact stud stresses the body in a direction not parallel to the main axis of the prosthesis and the at least one contact stud is movable relative to the body; and
   wherein the at least one contact stud has a lateral face extending outside the body.

14. Intervertebral disc prosthesis having a main axis, comprising:
   two plates, wherein at least one of the plates includes at least two contact studs arranged symmetrically about the main axis of the at least one plate; and
   a deformable body interposed between the plates, wherein upon movement of the at least one of the plates having the at least two contact studs, at least one of the at least two contact studs stresses the body in a direction not parallel to the main axis of the prosthesis and the at least one contact stud is slidably movable relative to the body.

15. Intervertebral disc prosthesis having a main axis, comprising:
   a first and second plate, each plate comprising at least one contact stud, the at least one contact stud of the first plate overlapping the at least one contact stud of the second plate by a length in a direction parallel to the main axis of the prosthesis when the prosthesis is not stressed.

16. Prosthesis according to claim 15, wherein the overlap length is between about 0.35 and about 0.65 of the distance separating the first and second plates when the prosthesis is not stressed.

17. Prosthesis according to claim 15 or 16, wherein the overlap length is between about 0.45 and 0.85 of the height of the contact studs parallel to the main axis of the prosthesis.

18. Prosthesis according to claim 1, 2 or 15, wherein each plate comprises at least two contact studs, the contact studs being arranged alternatingly around the main axis of the prosthesis.

19. Intervertebral disc prosthesis comprising:
   two plates;
   a deformable body interposed between the plates, wherein at least one of the plates comprises at least one contact stud movable in the body; and
   wherein the body defines a recess opening into a lateral face of the body and the at least one contact stud extends in the recess opening.

20. Intervertebral disc prosthesis comprising:
   two plates;
   a deformable body interposed between the plates, wherein at least one of the plates comprises at least one contact stud movable in the body; and
   wherein the at least one contact stud has a cylindrical lateral face, and the body has a cylindrical face bearing on the cylindrical face of the at least one contact stud.

21. Intervertebral disc prosthesis comprising:
   two plates;
   a deformable body interposed between the plates, wherein at least one of the plates comprises at least one contact stud movable in the body; and
   wherein the at least one contact stud has a lateral face extending outside the body.

* * * * *

UNITED STATES PATENT AND TRADEMARK OFFICE
CERTIFICATE OF CORRECTION

PATENT NO.    : 6,579,320 B1
DATED         : June 17, 2003
INVENTOR(S)   : Fabien Gauchet, Pierre Henri Saint-Martin and William J. Kelly It is certified that error appears in the above-identified patent and that said Letters Patent is hereby corrected as shown below:

Column 2,
Line 43, "test" should read -- rest --.

Column 5,
Line 26, before "slightly" insert -- are --.
Line 47, delete "shape of the prosthesis".
Line 47, after "bean" insert -- shaped --.
Line 47, after "and" insert -- since --.

Column 6,
Line 55, "is" should read -- are --.

Signed and Sealed this

Nineteenth Day of August, 2003

JAMES E. ROGAN
*Director of the United States Patent and Trademark Office*